US00PP30611P2

(12) United States Plant Patent
Hanes

(10) Patent No.: US PP30,611 P2
(45) Date of Patent: Jun. 25, 2019

(54) ***PELARGONIUM* PLANT NAMED 'PEQZ0047'**

(50) Latin Name: ***Pelargonium* interspecific**
Varietal Denomination: PEQZ0047

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,717

(22) Filed: Apr. 11, 2018

(51) Int. Cl.
*A01H 5/02* (2018.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — Dale Skalla

(57) ABSTRACT

A new *Pelargonium* plant named 'PEQZ0047' with dark red colored inflorescences held above the dark green foliage, very heat and drought tolerant with continuous color through the most extreme summer heat, and exceptional edema tolerance on a well-branched plant habit.

1 Drawing Sheet

Latin name of the genus and species of the plant claimed: *Pelargonium* interspecific.

Varietal denomination: 'PEQZ0047'.

BACKGROUND OF THE NEW PLANT

The present invention comprises a new *Pelargonium*, botanically known as *Pelargonium* interspecific, and hereinafter referred to by the variety name 'PEQZ0047'.

'PEQZ0047' is a product of a planned breeding program. The new cultivar 'PEQZ0047' has dark red colored inflorescences held above the dark green foliage, very heat and drought tolerant with continuous color through the most extreme summer heat, and exceptional edema tolerance on a well-branched plant habit.

'PEQZ0047' originates from a hybridization in a controlled breeding program made in September 2012, in a greenhouse in Guatemala. The female parent was an unpatented, proprietary plant of P. interspecific parentage, identified as '11062-2' with red color florets and dark green leaves.

The male parent of 'PEQZ0047' was an unpatented, proprietary plant of P. interspecific parentage, identified as '10817-1' with rose bicolored florets. The resultant seed was sown in November of 2012.

'PEQZ0047' was selected as one flowering plant within the progeny of the stated cross in March 2013 in a greenhouse in Gilroy, Calif.

The first act of asexual reproduction of 'PEQZ0047' was accomplished when vegetative cuttings were propagated from the initial selection in April 2013 in a greenhouse in Gilroy, Calif.

BRIEF SUMMARY OF INVENTION

Horticultural examination of plants grown from cuttings of the plant initiated in June 2013 in Gilroy, Calif., and continuing thereafter, has demonstrated that the combination of characteristics as herein disclosed for 'PEQZ0047' are firmly fixed and are retained through successive generations of asexual reproduction.

'PEQZ0047' has not been observed under all possible environmental conditions. The phenotype may vary significantly with variations in environment such as temperature, light intensity, and day length.

A Plant Breeder's Right for this cultivar has not been applied for. 'PEQZ0047' has not been made publicly available prior to the effective filing date of this application, notwithstanding any disclosure that may have been made less than one year prior to the effective filing date of this application by the inventor or another who obtained 'PEQZ0047' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0047' with colors being as true as possible with an illustration of this type.

Figure 1:
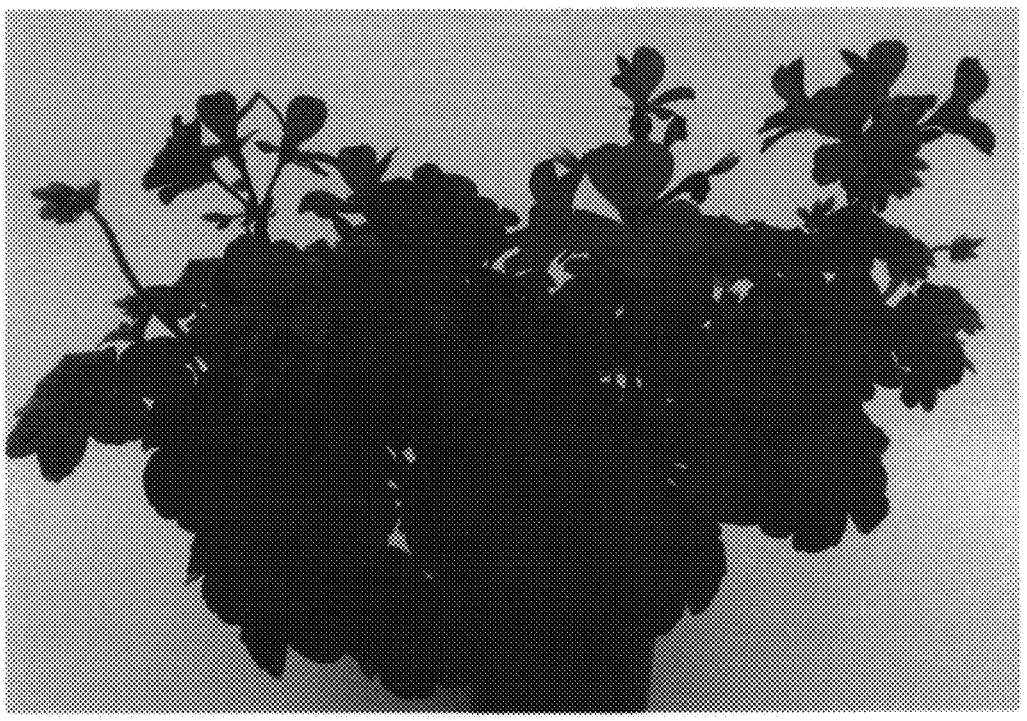
Figure 2:
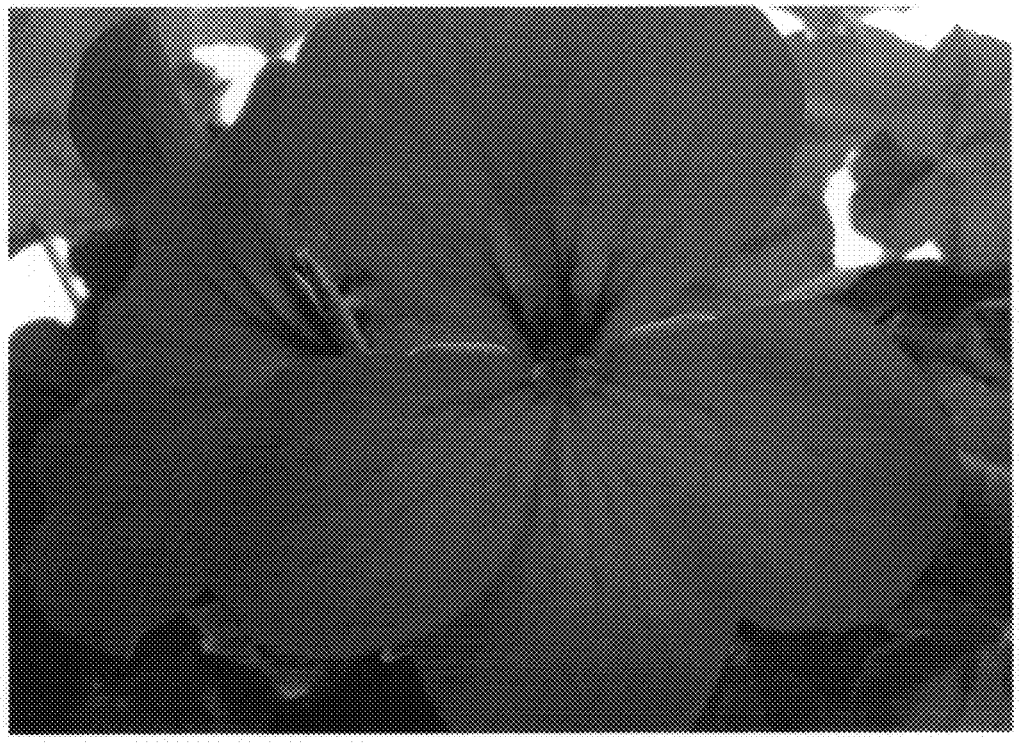

The photographic drawings show in FIG. 1, 3 flowering plants of the new variety and in FIG. 2, a close-up of an inflorescence.

DETAILED BOTANICAL DESCRIPTION

The plant descriptions, measurements, and photo were taken in Gilroy, Calif. in December 2017 under natural light. These plants were approximately 10 weeks old and were grown in a 4.5 inch pots, in a greenhouse trial.

Color references are made to The Royal Horticultural Society Colour Chart (R.H.S.) 20015.

TABLE 1

DIFFERENCES BETWEEN THE NEW VARIETY 'PEQZ0047' AND A MOST SIMILAR VARIETY

| | 'PEQZ0047' | 'Caliente Fire'(U.S. Pat. No. PP20,482) |
|---|---|---|
| Floret size: | Larger | Smaller |
| Flower: | Dark red and free-flowering | Dark red; fewer flowers |
| Plant growth: | Tends to spread and is more vigorous | More upright |

Plant:

*Form, growth and habit.*—Upright, outwardly spreading and rounded growth habit, heat and drought tolerant with continuous color through the most extreme summer heat, edema tolerance, well-branched plant habit.

*Plant height.*—17-18.0 cm.

*Plant height (inflorescence included).*—19-25.0 cm.

*Plant width.*—29-39.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—RHS 137A.

*Immature leaf, lower surface.*—RHS 137B.

*Mature leaf, color upper surface.*—RHS 139A.

*Mature leaf, color lower surface.*—RHS 139B.

*Length.*—7-8.0 cm.

*Width.*—6.5-9.5 cm.

*Shape.*—Cordate to orbicular.

*Base shape.*—Cordate.

*Apex shape.*—Acute to apiculate.

*Margin.*—Dentate to ciliate.

*Texture upper side.*—Hirsute.

*Texture lower side.*—Hirsute.

*Leaf zonation color.*—None.

*Color of veins, upper surface.*—RHS 137C.

*Color of veins, lower surface.*—RHS 137B.

*Pattern of veining.*—Palmate.

*Petiole color.*—RHS 137C.

*Petiole length.*—5.7-8.5 cm.

*Diameter of petiole.*—0.2 cm.

*Texture.*—Pilose, hirsute, glandular hairs.

Stem:

*Quantity of branches.*—3.

*Color of stem.*—Between RHS 144A/144B.

*Length of stem.*—15-20.0 cm.

*Diameter.*—0.5-0.8 cm.

*Length of internodes.*—2.5-4.0 cm.

*Texture.*—Sparsely hirsute, pilose, glandular hairs.

Peduncle:

*Color of peduncle.*—RHS 137B.

*Length of peduncle.*—11-14.0 cm.

*Peduncle diameter.*—0.3-0.35 cm.

*Texture.*—Hirsute, glandular hairs.

Pedicel:

*Color of pedicel.*—RHS 153A.

*Length of pedicel.*—2.6-3.2 cm.

*Diameter of pedicel.*—0.15-0.2 cm.

*Texture.*—Sparsely pilose, glandular hairs.

Bud (just before opening):

*Color.*—RHS 53A.

*Length.*—2.5 cm.

*Width.*—0.8-1.0 cm.

*Shape.*—Elliptical.

Inflorescence:

*Type.*–Umbel; semi-spherical or nearly semi-spherical.

*Lastingness of individual flowers.*—7-9 days at 18° C. temperature.

*Number of inflorescences per plant.*—13, with 7 immature umbels and 6 mature.

*Fragrance.*—None.

*Umbel diameter.*—7-9.0 cm.

*Umbel depth.*—8-9.0 cm.

Corolla:

*Form.*—Single.

*Number of petals.*—5.

*Diameter of flower.*—4.5-5.0 cm.

*Depth of flower.*—2-2.5 cm.

*Color upper petals, upper surface.*—Closest to RHS 46A with RHS 202A veining.

*Color upper petals, lower surface.*—Closest to RHS 45A with RHS 202A veining.

*Length of upper petals.*—3.4-3.6 cm.

*Width of upper petals.*—2-2.2 cm.

*Color lower petals, upper surface.*—Closest to RHS 46A.

*Color lower petals, lower surface.*—Closest to RHS 45B.

*Length of lower petals.*—3-3.2 cm.

*Width of lower petals.*—2.1-2.3 cm.

*Petal shape.*—Obovate to orbicular.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A.

*Length of sepals.*—1.2-1.4 cm.

*Width of sepals.*—0.3-0.5 cm.

*Sepal shape.*—Lanceolate to linear.

*Apex shape.*—Acute to apiculate.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.7-0.8 cm.

*Style color.*—Closest to RHS 45A.

*Style length.*—0.4 cm.

*Stigma color.*—Closest to RHS 52A.

*Ovary color.*—RHS 141A.

*Ovary length.*—0.3-0.4 cm.

*Ovary diameter.*—0.2 cm.

Androecium:

*Number of stamens.*—7-9.

*Color of filaments.*—RHS 54A with RHS NN155D basally.

*Length filaments.*—0.6-0.7 cm.

*Anther color.*—RHS N77A.

*Length of anthers.*—0.2 cm.

*Color of pollen.*—RHS N25B.

*Pollen amount.*—Normal.

*Fertility/seed set.*—Few.

*Disease/pest resistance.*—Has not been determined to date.

What is claimed is:

1. A new and distinct variety of *Pelargonium* plant named 'PEQZ0047' substantially as illustrated and described herein.

* * * * *